United States Patent [19]

Bomback et al.

[11] Patent Number: 4,755,049

[45] Date of Patent: Jul. 5, 1988

[54] METHOD AND APPARATUS FOR MEASURING THE ION IMPLANT DOSAGE IN A SEMICONDUCTOR CRYSTAL

[75] Inventors: John L. Bomback, Plymouth; John V. James, Canton; Charles C. Wang, Bloomfield Hills, all of Mich.

[73] Assignee: Ford Motor Company, Dearborn, Mich.

[21] Appl. No.: 937,158

[22] Filed: Dec. 2, 1986

[51] Int. Cl.$^4$ ............................................ G01N 21/84
[52] U.S. Cl. ..................................... 356/30; 356/318; 356/417
[58] Field of Search ................. 356/30, 315, 417, 318; 307/427

[56] References Cited

PUBLICATIONS

Study of Optical Third–Harmonic Generation in Reflection; by C. C. Wang et al; pp. 1079–1082; Physical Review, vol. 185, No. 3, 9/15/69.
A New Ion Dose Uniformity Measurement Technique; by J. C. Cheng et al; pp. 143–152; Solid State Technology, 11/83.
Characterization of Ion Implanted Silicon—Applications for IC Process Control; by M. Markert et al; pp. 101–106; S. S. Tech., 11/83.
High Resolution Dose Uniformity Monitoring of Ion Implanters, Part I; by J. R. Golin et al; pp. 137–141; S. S. Tech., 8/84.
High Resolution Dose Uniformity Monitoring of Ion Implanters, Part II; by J. R. Golin et al; pp. 289–296; S. S. Tech., 9/84.
Advances in Data Management for Implantation Process Control; by D. S. Perloff et al; pp. 129–135; S. S. Tech., 2/85.
A Performance Survey of Production Ion Implanters; by M. I. Current et al; pp. 139–146; S. S. Tech., 2/85.
Advances in Sheet Resistance Measurements for Ion Implant Monitoring, by W. A. Keenan et al; pp. 143–148; S. S. Tech., 6/85.
Advanced Methods of Ion Implant Monitoring Using Optical Dosimetry; by J. R. Golin et al.; pp. 155–163; S. S. Tech., 6/85.
Low Dose Ion Implant Monitoring; by R. O. Deming et al; pp. 163–167; S. S. Tech., 9/85.
Ion Implant Monitoring with Thermal Wave Technology; by W. L. Smith et al; pp. 85–92; S. S. Tech., 1/86.
Nonlinear Optical Materials; edited by D. A. B. Miller; Fall Meeting of the Materials Research Society; Dec. 4–6, 1985; pp. 131–133.
Bulletin of the Amer. Phys. Soc.; Mar. 1985, vol. 30, No. 3; p. 574.
Mapping of Ion Implanted Wafers; by M. I. Current et al; pp. 487–536; 1984 Academic Press.
Bulletin–Model 4400 Signal Processing System; by EG&G Princeton Applied Research (11 pages) 1983.

Primary Examiner—Craig E. Church
Assistant Examiner—Jack I. Berman
Attorney, Agent, or Firm—Paul K. Godwin, Jr.; Clifford L. Sadler

[57] ABSTRACT

A technique for measuring the ion implant dosage involves method and apparatus for directing pulses of coherent radiation from a laser to the surface of a semiconductor that has been subjected to ion implant. The intensity of the third harmonic reflected from the semiconductor is determined and correlated to determine the ion dosage within the semiconductor.

6 Claims, 2 Drawing Sheets

METHOD AND APPARATUS FOR MEASURING THE ION IMPLANT DOSAGE IN A SEMICONDUCTOR CRYSTAL

BACKGROUND OF THE INVENTION

1. Field of the Invention

The present invention is directed to the field of semiconductor manufacturing and more specifically to the area of ion dose measurements performed during the manufacturing process.

2. Description of the Prior Art

Ion implantation is a common semiconductor processing step used to modify the near-surface chemical and physical composition of a wafer by the injection of high energy ions. The crystal lattice of the semiconductor is damaged by the ion injection process. Normally, the ion beam is small (5 mm), compared with the size of the wafer (75–200 mm). Therefore, the scanning of the ion beam with respect to the wafer is necessary to achieve a uniform ion dose. Variation in ion dose may occur over the wafer surface due to a number of factors including improper scanning, wafer charging or beam instability. Of course such variation in the ion dose will give rise to variation in the electrical properties of the semiconductor device being fabricated. Variation in the ion dose then, in turn, has a direct impact on the quality yield. Accordingly, techniques have been developed that give an estimation as to ion dose and in some cases the uniformity of the dose.

One of the known measurement techniques involves direct sheet resistance. In that method, the wafer is subjected to a high temperature annealing step in order to eliminate lattice damage and to activate the implanted ions. Subsequently, a collinear four point probe is placed into electrical contact with the wafer surface and current is forced through two of the probes. Voltage is then measured across the other two probes and a resistance reading is made.

Another method utilizes thermal waves that are propagated into the wafer. In that method, high frequency pulses of laser energy are directed to be incident on the semiconductor surface and establish a train of thermal waves that propagate into the wafer. The surface temperature of the wafer is modulated as these waves are scattered by subsurface, implant induced damage. The wafer surface temperature is monitored by the reflection of a second laser beam, thus giving a signal related to ion dose.

An indirect method of measuring ion dose is termed optical dosimetry. In that method, a glass wafer coated with a photo-resist layer is used in the implanter as a dummy test piece. In that test piece, high implantation results in darkening of the photo-resist layer. As a result, the transmission of collimated light directed through the photo-resist is affected and may be measured as a relation of the ion dose.

SUMMARY OF THE INVENTION

It is an object of the present invention to provide a noncontacting and nondestructive method and apparatus for directly measuring the ion dose in an ion implanted semiconductor crystal.

It is another object of the present invention to provide a measuring technique whereby the ion dosage can be determined during processing of semiconductor wafers prior to annealing so as to detect flaws in the ion implant stage of the process prior, to completing the fabrication process.

It is still another object of the present invention to provide a measuring technique that is ideally suited for automation within a semiconductor production process so as to monitor quality and provide instantaneous feedback as to variations in ion dosage.

It is a further object of the present invention to provide an ion dose measuring system that is applicable to any crystal and semiconductor material including silicon, germanium, gallium arsenide and indium phosphide.

It is a still further object of the present invention to provide an ion dose measuring technique which utilizes a source of coherent light energy directed at the surface of an ion implanted semiconductor crystal and to sense and measure the intensity of the third harmonic of the light energy reflected from the crystal structure of the semiconductor.

BRIEF DESCRIPTION OF THE DRAWINGS

FIG. 4 illustrates a test wafer with prescribed ion dose boundaries.

FIG. 5 is a map of the measurements made on the test wafer shown in FIG. 4 utilizing the apparatus shown in FIG. 1.

DESCRIPTION OF THE PREFERRED EMBODIMENT

Figure 1:
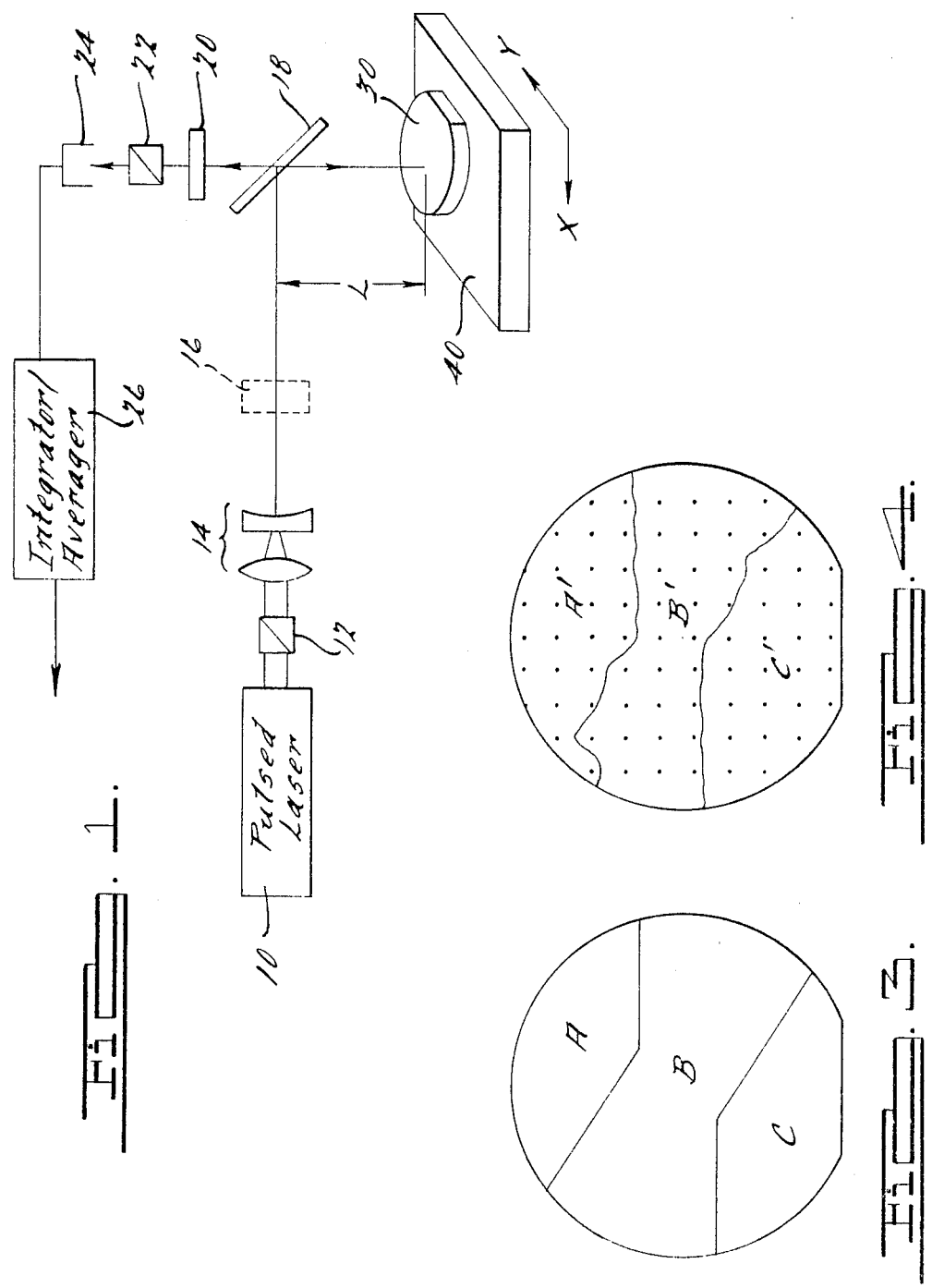
FIG. 1 illustrates an embodiment of the apparatus employed in the present invention.

In the embodiment shown in FIG. 1, a Q-switched, Nd:YAG laser 10 is provided which generates 4 ns pulses at a 10 Hz rate with a fundamental wavelength of 1.06$\mu$. The beam of pulsed energy produced by the laser 10 is directed through a polarizer 12 and collimating optics 14. The collimated beam is directed to a dichroic mirror 18 where it is reflected onto the surface of a semiconductor wafer 30. The wafer 30 is normally placed on an X-Y movable fixture in order that multiple sample measurements can be made across the surface of the semiconductor crystal 30. An alternative apparatus configuration may provide for a scanning beam and a fixed semiconductor wafer.

As the pulses of beam energy impinge onto the semiconductor crystal 30, harmonics of the fundamental wavelength are caused to be reflected by the nonlinear optical property of the semiconductor 30. For instance, the second harmonic of the fundamental wavelength is produced. It has been found that the second harmonic generally emitted from centrosymmetric crystals, such as silicon, is limited to the top several atomic layers of the crystal. On the other hand, Applicants have found that the third harmonic is generated at depths from the surface of the crystal which are governed by the absorption length of the fundamental wavelength or that of the third harmonic. The probed depth corresponding to an absorption length of approximately 10 nm into the surface of the semiconductor crystal corresponds to the volume of material normally modified by implantation of ions. The lattice damage caused by the ion implantation process affects the intensity of the third harmonic generation, as compared to the pure crystal structure. As such, variations in the ion dose will appear as measured variations in these third harmonic emissions from the surface of the semiconductor crystal 30.

The dichroic mirror 18, in the embodiment shown in FIG. 1, is selected to reflect the fundamental wavelength and transmit the third harmonic of the fundamental. The third harmonic emitted from the semiconductor crystal 30 is transmitted through the dichroic mirror 18, a filter 20 and a polarizer 22 to a sensor 24. In this case, the sensor 24 is a photomultiplier tube which provides an electrical output signal that corresponds to the intensity of the third harmonic of the fundamental frequency available at the sensor 24. The output of photomultiplier 24 is fed to an integrater/averager system 26 such as is commercially available. The integrater/averager employed in the experiments leading up to the present invention was a Model 4400 Signal Processing System produced by EG&G Princeton Applied Research of Princeton, N.J.

The function of the integrater/averager 26 is to analyze the pulsed output of the photo multiplier sensor 24 and to provide an output indicating the relative intensity of the third harmonic at the sensor.

The distance indicated as "L" between the surface of the semiconductor crystal 30 and the point on the dichroic mirror 18 at which the beam is reflected towards the semiconductor is an important consideration when the medium between those two points is air. In a vacuum, the distance "L" is arbitrary. However, in an air medium, a third harmonic is generated by the air and dispersion causes intensity variations of a sinusoidal nature to occur in the path between the dichroic mirror 18 and the semiconductor 30. It has been found that when "L" equals an even number of coherence lengths of the third harmonic generated in air, the most consistent measurements occur which closely approximate utilizing a vacuum medium.

The fact that air can be used as a medium in performing the aforementioned measurement makes such measurements highly suited to automated production utilization.

Figure 2:
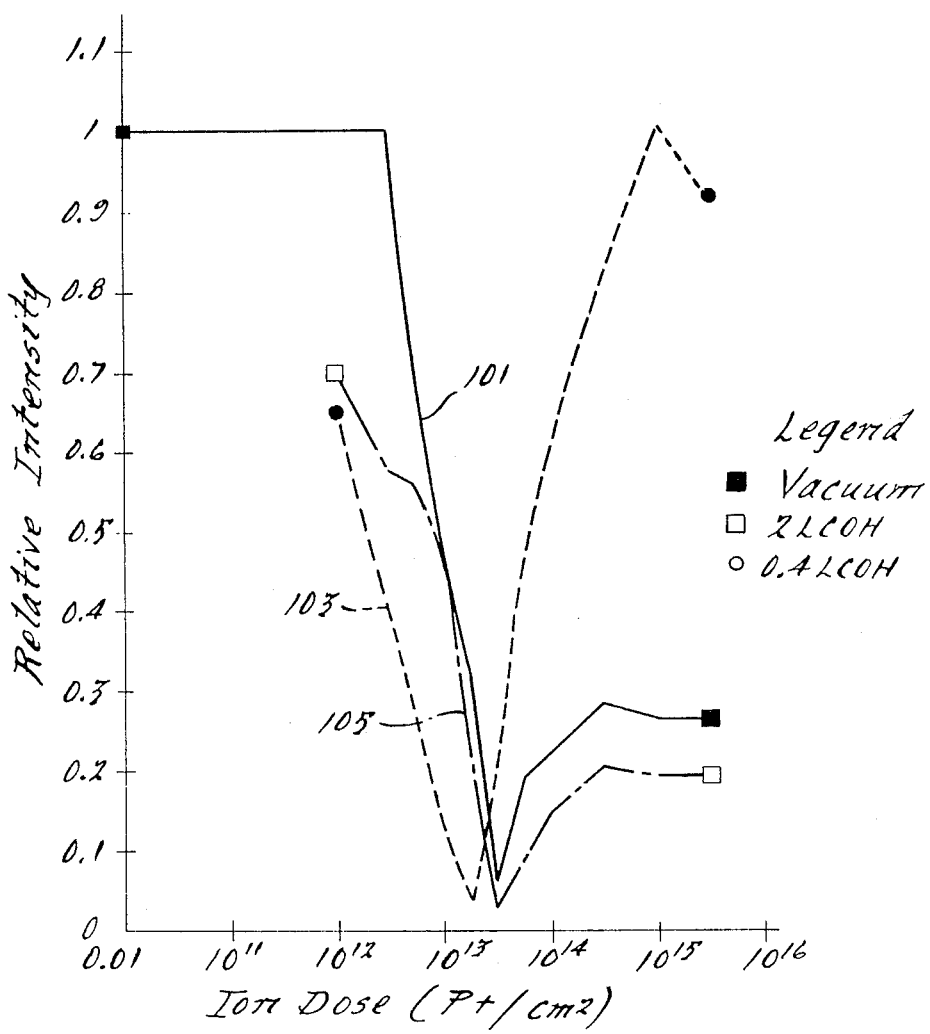
FIG. 2 is a plot of ion dose intensity measurements taken with the apparatus shown in FIG. 1, in vacuum and air mediums.

The graph in FIG. 2 illustrates the results of comparing measurements taken using the aforementioned apparatus of various samples in which ion doses are within the range indicated. The continuous line 101 indicates the measurements taken of the various samples in a vacuum medium. The short dashed line 103 indicates the same samples made in an air medium in which the distance between the mirror 18 and the surfaces of the samples was approximately 0.4 coherence lengths for third harmonic generation ($L_{coh}$). The long dashed line 105 indicates the same samples measured by the aforementioned apparatus wherein the distance "L" between the mirror 18 and the top surfaces of the samples was equal to 2 $L_{coh}$.

It can be seen from FIG. 2 that by utilizing an even number of $L_{coh}$ as the value for "L", the use of the apparatus in air will be approximately equivalent to the results when used in a vacuum.

FIG. 3 illustrates a sample wafer defining three zones of ion imPlant having distinct doses of 50 KEV P+ ions. In zone "A", the dose is $3 \times 10^{13}$ cm$^{-2}$, while the dose in zone "B" is $1.8 \times 10^{13}$ cm$^{-2}$ and the dose in zone "C" is $5.6 \times 10^{13}$ cm$^{-2}$.

FIG. 4 illustrates a map of measurements taken of the sample shown in FIG. 3 utilizing a range of relative intensities of the measured third harmonic to define the boundary regions A', B' and C'.

While the aforementioned apparatus describes the use of a polarizer 12 and an analyzer 22 in association with the sampling pulses, it should be pointed out that rotational movement of the semiconductor wafer 30 will cause variations in the sensed third harmonic reflected to the sensor 24. Accordingly, it may be desirable to utilize a quarter wave plate such as that shown in phantom lines and designated as 16 in FIG. 1 to provide circular polarization of the beam and eliminate the orientation variations.

The intensity of the pulse energy from the laser source 10 was selected in the present invention to have a pulse energy of approximately 40 mJ. The energy was selected to be well below the annealing threshold for the implant amorphized silicon crystal but at the same time high enough to cause a third harmonic generation in the crystal surface that is easily detectable by the sensor 24. Certain variables in the present invention provide for added flexibility. For instance, the probed depth of effective measurement in the semiconductor crystal can be controlled by the selected wavelength of the fundamental radiation. On the other hand shorter pulse widths are preferable since higher power pulses may be available while maintaining the average energy below the annealing threshold. In addition, higher pulse rates are preferable in order to reduce the analysis time.

It will be apparent that many modifications and variations may be implemented without departing from the scope of the novel concept of this invention. Therefore, it is intended by the appended claims to cover all such modifications and variations which fall within the true spirit and scope of the invention.

We claim:

1. A method of measuring the ion implantation dose of a semiconductor crystal, comprising the steps of:
    providing a source to generate a beam of coherent light energy at a predetermined fundamental wavelength;
    pulsing said coherent light energy beam to provide pulses of light energy having a predetermined pulse width and repetition rate;
    directing said pulsed coherent light energy beam onto a defined area of said semiconductor crystal;
    sensing the third harmonic of said fundamental wavelength reflected from said defined area of said semiconductor crystal;
    measuring the intensity of said third harmonic of energy reflected from said semiconductor crystal; and
    determining the ion implantation dose based on the measured intensity of the third harmonic of energy reflected from said crystal.

2. A method as in claim 1, wherein said step of directing includes providing a dichroic mirror that is also located between said beam source and said semiconductor crystal, oriented to reflect said fundamental wavelength towards said semiconductor crystal and to transmit said third harmonic of said fundamental wavelength.

3. A method as in claim 2, wherein said step of sensing includes the step of providing means for sensing light energy and said dichroic mirror is provided and located between said sensing means and said semiconductor crystal to transmit only the third harmonic of said fundamental wavelength to said sensing means.

4. A method as in claim 3, wherein said step of directing is performed to direct said beam of coherent light energy to have an angle of incidence that is normal to the surface of the semiconductor crystal.

5. A method as in claim 4, wherein said sensing means is provided to receive the third harmonic of said fundamental wavelength reflected from said semiconductor crystal in a direction normal to the semiconductor crystal surface.

6. A method as in claim 5, wherein the medium between the directing means and the surface of the semiconductor crystal is air and the dichroic mirror is provided at a distance from the surface of the semiconductor crystal that is equal to an even multiple of the coherence length for third harmonic generation in air.

* * * * *